United States Patent
Saito

(10) Patent No.: US 10,327,961 B2
(45) Date of Patent: Jun. 25, 2019

(54) ABSORBENT ARTICLE

(71) Applicant: UNICHARM CORPORATION, Ehime (JP)

(72) Inventor: Kyota Saito, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 16/066,319

(22) PCT Filed: Sep. 12, 2016

(86) PCT No.: PCT/JP2016/076757
§ 371 (c)(1),
(2) Date: Jun. 27, 2018

(87) PCT Pub. No.: WO2017/115498
PCT Pub. Date: Jul. 6, 2017

(65) Prior Publication Data
US 2019/0015265 A1     Jan. 17, 2019

(30) Foreign Application Priority Data

Dec. 28, 2015   (JP) .................................. 2015-256831

(51) Int. Cl.
*A61F 13/62* (2006.01)
*A61F 13/56* (2006.01)
(Continued)

(52) U.S. Cl.
CPC ...... *A61F 13/49011* (2013.01); *A61F 13/496* (2013.01); *A61F 13/4963* (2013.01);
(Continued)

(58) Field of Classification Search
CPC ............ A61F 13/49011; A61F 13/5638; A61F 13/5655; A61F 13/49058; A61F 13/622
(Continued)

(56) References Cited

U.S. PATENT DOCUMENTS

2002/0138065 A1* 9/2002 Yeater ............... A61F 13/49011
604/395
2002/0151858 A1* 10/2002 Karami ................... A61F 13/49
604/385.3
(Continued)

FOREIGN PATENT DOCUMENTS

CN        101043862 A    9/2007
CN        101803976 A    8/2010
(Continued)

OTHER PUBLICATIONS

International Search Report for PCT/JP2016/076757, dated Nov. 29, 2016, 3 pages.
(Continued)

*Primary Examiner* — Susan S Su
(74) *Attorney, Agent, or Firm* — Hauptman Ham, LLP

(57) ABSTRACT

An absorbent article includes a front waist portion, a back waist portion and a crotch portion between the front waist portion and the back waist portion. A one-side end portion of the back waist portion on a one side in a lateral direction is joined to a one-side end portion of the front waist portion on the one side in the lateral direction. The back waist portion includes a fastening portion on another side in the lateral direction. The back waist portion includes an elastic region in at least an upper end portion. A lateral distance between a one-side end of the elastic region on the one-side and the center of the crotch portion is smaller than a lateral distance between an other-side end of the elastic region on the other side and the center of the crotch portion.

9 Claims, 7 Drawing Sheets

(51) Int. Cl.
*A61F 13/49* (2006.01)
*A61F 13/496* (2006.01)

(52) U.S. Cl.
CPC ...... *A61F 13/5638* (2013.01); *A61F 13/5655* (2013.01); *A61F 13/49017* (2013.01); *A61F 13/49058* (2013.01); *A61F 13/565* (2013.01); *A61F 13/622* (2013.01)

(58) Field of Classification Search
USPC .............................. 604/391, 392, 395, 396
See application file for complete search history.

(56) References Cited

U.S. PATENT DOCUMENTS

2011/0184372 A1* 7/2011 Esping Ostlin ... A61F 13/49012
604/392
2017/0319397 A1* 11/2017 Desai ................ A61F 13/49001

FOREIGN PATENT DOCUMENTS

| JP | H4-5826 U | 1/1992 |
| JP | H6-63077 A | 3/1994 |
| JP | 2000-27004 A | 1/2000 |
| JP | 2008-104874 A | 5/2008 |
| JP | 2010-5270 A | 1/2010 |
| JP | 2018-512 A | 1/2018 |
| JP | 2018-68898 A | 5/2018 |
| WO | 2007/024928 A1 | 3/2007 |

OTHER PUBLICATIONS

International Preliminary Report on Patentability in PCT Application No. PCT/JP2016/076757, dated Nov. 29, 2016, 9pp.
Extended European Search Report in EP Application No. 16881478.8, dated Dec. 12, 2018, 5pp.
Office Action in CN Application No. 201680076505.3, dated Mar. 5, 2019, 10pp.

* cited by examiner

ABSORBENT ARTICLE

RELATED APPLICATIONS

The present application is a National Phase of International Application Number PCT/JP2016/076757, filed Sep. 12, 2016, and claims priority to Japanese Application Number 2015-256831, filed Dec. 28, 2015.

TECHNICAL FIELD

The present invention relates to an absorbent article.

BACKGROUND ART

A disposable diaper such as a so-called tape-type diaper or an underpants-shaped disposable diaper is conventionally known as an absorbent article for absorbing excrement. These tape-type diapers and underpants-shaped disposable diapers have a problem of difficulty in being put on a wriggling infant and a problem that the diapers force a wearer to take an unnatural posture when being put on. In order to solve these problems, PTL 1 describes a disposable diaper 1 in which portions on either one side of the left or right sides of the waist part are joined together, and portions on the other side are not joined together.

CITATION LIST

Patent Literature

Japanese Unexamined Utility Model Application Publication No. H4-5826

SUMMARY OF INVENTION

Technical Problem

However, in a disposable diaper 1 described in PTL 1, while one of wearer's legs being inserted into a leg hole 11 of either one side of the left or right sides of the waist part, the front and back waist parts 5A and 5C on other side are pulled together so as to overlap, and then the front and back waist parts are joined. Accordingly, there is a possibility that, if only one of the wearer's legs is inserted, an absorbent body 4 which has been located at the center of the wearer's body shifts on the other side due to waist part 5A being pulled.

The present invention was achieved in light of the problems described above, and an aspect of the present invention is to suppress displacement of the crotch portion of an absorbent article from the center of the wearer's body.

Solution to Problem

An aspect of the invention to achieve the above advantage is an absorbent article having a longitudinal direction, a lateral direction intersecting the longitudinal direction, and a front-back direction intersecting the longitudinal direction and the lateral direction, the absorbent article including: a front waist portion extending along the lateral direction; a back waist portion extending along the lateral direction; and a crotch portion provided between the front waist portion and the back waist portion, a one-side end portion of the back waist portion on a one side in the lateral direction being joined to a one-side end portion of the front waist portion on the one side in the lateral direction, the back waist portion including a fastening portion on another side in the lateral direction, when putting on the absorbent article, the fastening portion projecting laterally from the back waist portion and being capable of being fastened to the front waist portion, the back waist portion including an elastic region in at least an upper end portion, the elastic region extending along the lateral direction, a lateral distance between a lateral one-side end of the elastic region on the one side and a lateral center of the crotch portion being smaller than a lateral distance between a lateral other-side end of the elastic region on the other side and the lateral center of the crotch portion.

Other features of the present invention will become apparent from the description of the present specification and the accompanying drawings.

Advantageous Effects of Invention

When only one of the wearer's legs is inserted and the crotch portion is positioned on the center of the wearer's body, the elastic region is stretched by pulling the other side of the back waist portion, causing the crotch portion to shift to the other side. However, anticipating the shift, an elastic region provided in the upper end portion of each waist portion and extending along lateral direction is made so that the distance between the one-side end and the center of the crotch portion is smaller than the distance between the other-side end and the center of the crotch portion. This makes it possible to suppress displacement of the crotch portion from the center of the wearer's body.

BRIEF DESCRIPTION OF DRAWINGS

FIG. 5B is a plan view of the diaper 1 in an unfolded manner, when the diaper 1 is put on.

DESCRIPTION OF EMBODIMENTS

Figure 1:
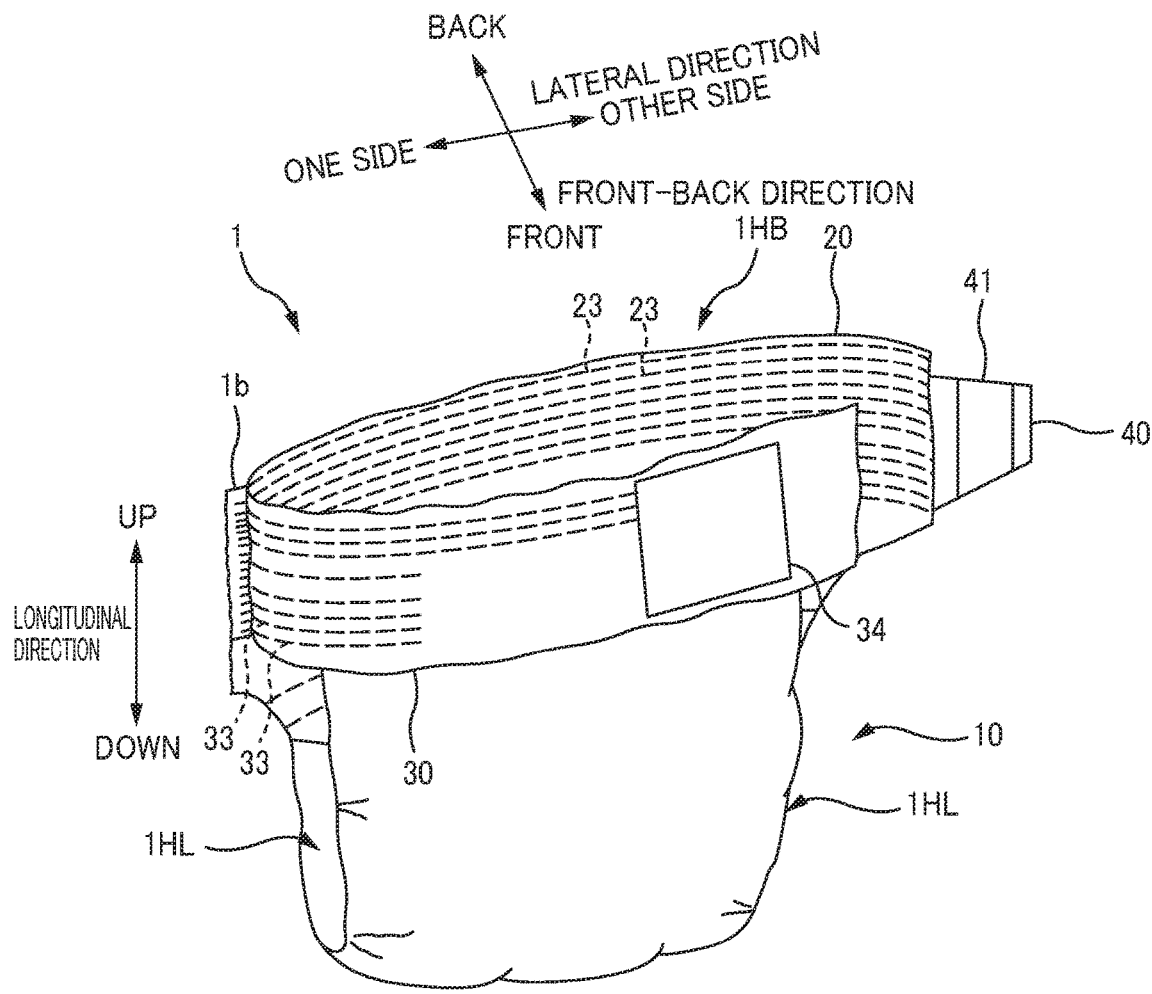
FIG. 1 is a schematic perspective view of a disposable diaper 1 according to an embodiment.

At least the following matters will be made clear by the description in the present specification and the accompanying drawings.

An absorbent article having a longitudinal direction, a lateral direction intersecting the longitudinal direction, and a front-back direction intersecting the longitudinal direction and the lateral direction, the absorbent article including: a front waist portion extending along the lateral direction; a back waist portion extending along the lateral direction; and a crotch portion provided between the front waist portion and the back waist portion, a one-side end portion of the back waist portion on a one side in the lateral direction being joined to a one-side end portion of the front waist portion on the one side in the lateral direction, the back waist portion including a fastening portion on another side in the lateral direction, when putting on the absorbent article, the fastening portion projecting laterally from the back waist portion and being capable of being fastened to the front waist portion, the back waist portion including an elastic region in at least an upper end portion, the elastic region extending along the lateral direction, a lateral distance between a lateral one-side end of the elastic region on the one side and a lateral center of the crotch portion being smaller than a lateral distance between a lateral other-side end of the elastic region on the other side and the lateral center of the crotch portion.

When only one of the wearer's legs is inserted and the crotch portion is positioned on the center of the wearer's body, the elastic region is stretched by pulling the other side of the back waist portion, causing the crotch portion to shift to the other side. However, with such an absorbent article, anticipating the shift, an elastic region provided in the upper end portion of each waist portion and extending along lateral direction is made so that the distance between the one-side end and the center of the crotch portion is smaller than the distance between the other-side end and the center of the crotch portion. This makes it possible to suppress displacement of the crotch portion from the center of the wearer's body.

In such an absorbent article, it is desirable
that, in the front waist portion, a region from the one-side end portion to the lateral center of the crotch portion includes an elastic region extending along the lateral direction, and
that a region from the other-side end portion to the lateral center of the crotch portion does not include an elastic region.

With such an absorbent article, the region of the front waist portion from the one-side end to the lateral center of the crotch portion includes the front elastic region. This improves the fit of the absorbent article. The region of the front waist portion from the other-side end to the lateral center of the crotch portion does not include the front elastic member. This can reduce a possibility that stretching/contracting of the front elastic region makes it easier to remove the fastening.

In such an absorbent article, it is desirable that a lateral distance between the lateral center of the crotch portion and a lateral one-side end of a longitudinal upper end of the front waist portion is larger than a lateral distance between the lateral center of the crotch portion and a lateral other-side end of the longitudinal upper end of the front waist portion.

With such an absorbent article, it is possible to reduce a region of the front waist portion onto which the back waist portion is stacked when fastening the other side by the fastening portion. This makes it possible to reduce wearer's discomfort which is caused by stacking of the back waist portion and the front waist portion during a period when putting on the diaper.

In such an absorbent article, it is desirable that a lateral distance from a lateral center of the back waist portion to the lateral center of the crotch portion is smaller than a difference between a lateral distance from a lateral other-side end to the lateral center of the crotch portion and a lateral distance from a lateral one-side end to the center of the crotch portion.

With such an absorbent article, in the lateral direction, the distance from the center of the back waist portion to the center of the crotch portion is smaller than the difference between the distance from the other-side end of the upper end of the back waist portion to the center of crotch portion and the distance from the one-side end of the upper end of the back waist portion to the center of crotch portion. This can further reduce a possibility that, when fastening the fastening portion to the front waist portion, the lateral center of the crotch portion is positioned away from the lateral center of wearer's crotch.

In such an absorbent article, it is desirable
that, in the back waist portion, the elastic region is a region in which a plurality of elastic strings are provided, and
that a number of elastic strings in an elastic region included between the lateral other-side end of the elastic region and the lateral center of the crotch portion is larger than a number of elastic strings in an elastic region included between the lateral one-side end of the elastic region and the lateral center of the crotch portion.

With such an absorbent article, a larger number of elastic strings is provided between the other-side end of the back waist portion and the lateral center of the crotch portion, than between the one-side end of the back waist portion and the lateral center of the crotch portion. This makes it possible to improve the fit around the wearer's waist.

In such an absorbent article, it is desirable
that the back waist portion includes a fastening member having the fastening portion,
that the fastening member is fixed to an other-side end portion of the back waist portion in a fixing region of the back waist portion, and
that a longitudinal length of the fixing region is equal to or larger than half a longitudinal length of an other-side end of the back waist portion.

With such an absorbent article, the longitudinal length of the fixing region is equal to or larger than half the longitudinal length of the other-side end of the back waist portion. This makes it possible to apply a force for pulling the fastening portion when putting on the absorbent article, to an region corresponding to a length equal to or larger than half the length of the end of the back waist portion.

In such an absorbent article, it is desirable
that the back waist portion, the front waist portion, and the crotch portion are individual components,
that a lower end of the back waist portion includes on the one side a one-side inclined portion that is inclined toward the one-side end portion,
that the lower end of the back waist portion includes on the other side an other-side inclined portion that is inclined toward the other-side end portion, and
that a lateral length of the one side inclined portion is larger than a lateral length of the other side inclined portion.

Such an absorbent article is able to be adjusted, by the fastening portion provided on the other side, to the size of the circumference of a wearer's leg. This makes it possible to achieve better fit of the absorbent article.

In such an absorbent article, it is desirable
that the back waist portion, the front waist portion, and the crotch portion are individual components,
that a first stacking region in which the crotch portion and the back waist portion are stacked is provided in a back side of the crotch portion in the front-back direction,
that a second stacking region in which the crotch portion and the front waist portion are stacked is provided in a front side of the crotch portion in the front-back direction, and that a length of an other-side end of the back waist portion is smaller than half a length of the crotch portion from a lower end of the first stacking region to a lower end of the second stacking region.

With such an absorbent article, the leg opening is enlarged so as to easily insert wearer's leg, and the other-side end of the back waist portion is shortened. This makes it easier to pull the fastening portion and the entirety of the back waist portion when fastening, making it easier to put on the absorbent article.

In such an absorbent article, it is desirable that the elastic region in the upper end portion is continuous in the lateral direction at least from a one end of the crotch portion to another end of the crotch portion.

With such an absorbent article, the elastic region in the upper end portion is continuous in the lateral direction at least from the one end of the crotch portion to the other end of the crotch portion. This can further reduce a possibility that, when fastening the fastening portion to the front waist portion, the lateral center of the crotch portion is positioned away from the lateral center of wearer's crotch.

Present Embodiment

Disposable Diaper 1 according to Present Embodiment

Figure 2:
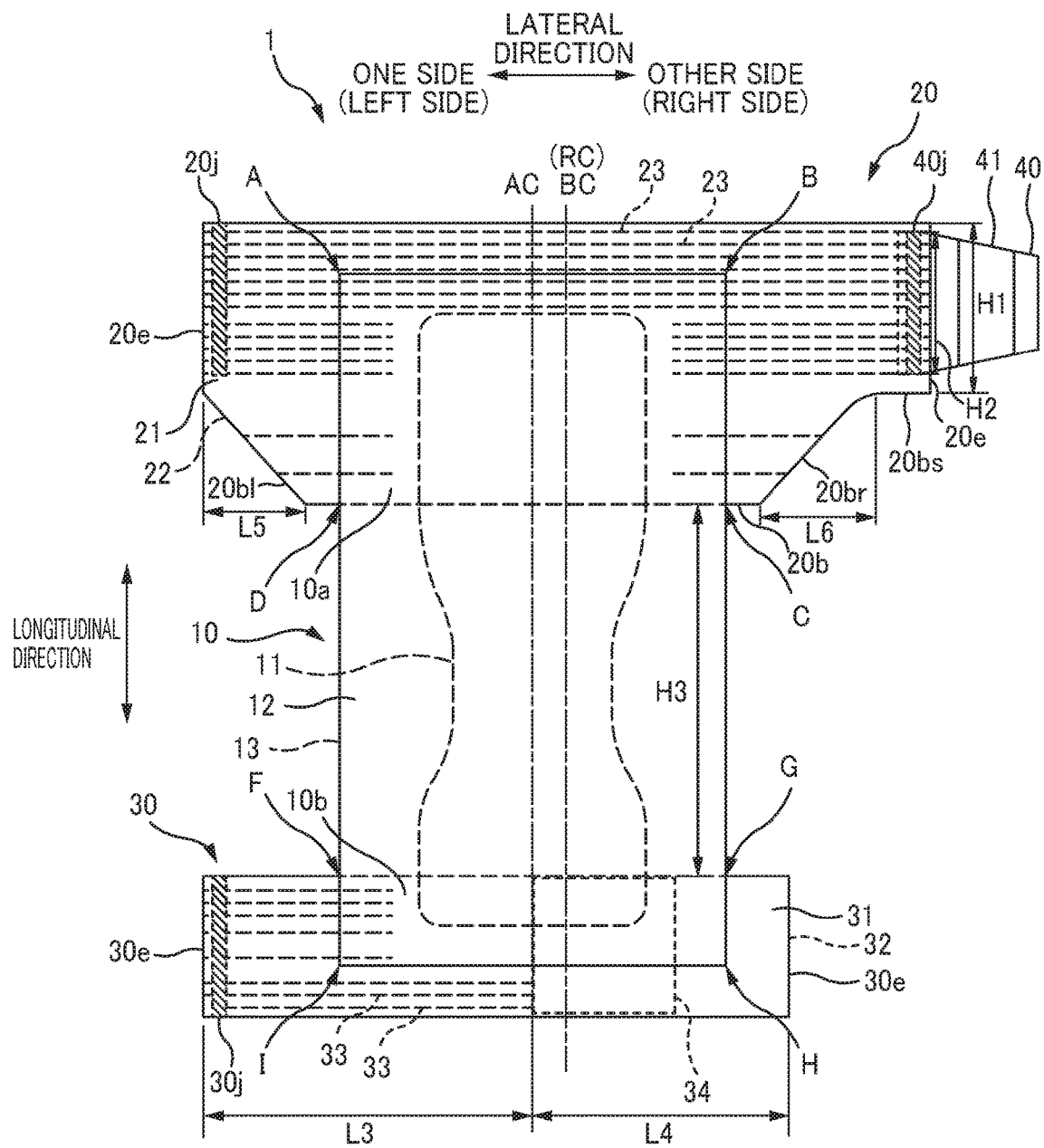
FIG. 2 is a plan view of the diaper 1 in an unfolded state.
Figure 3:
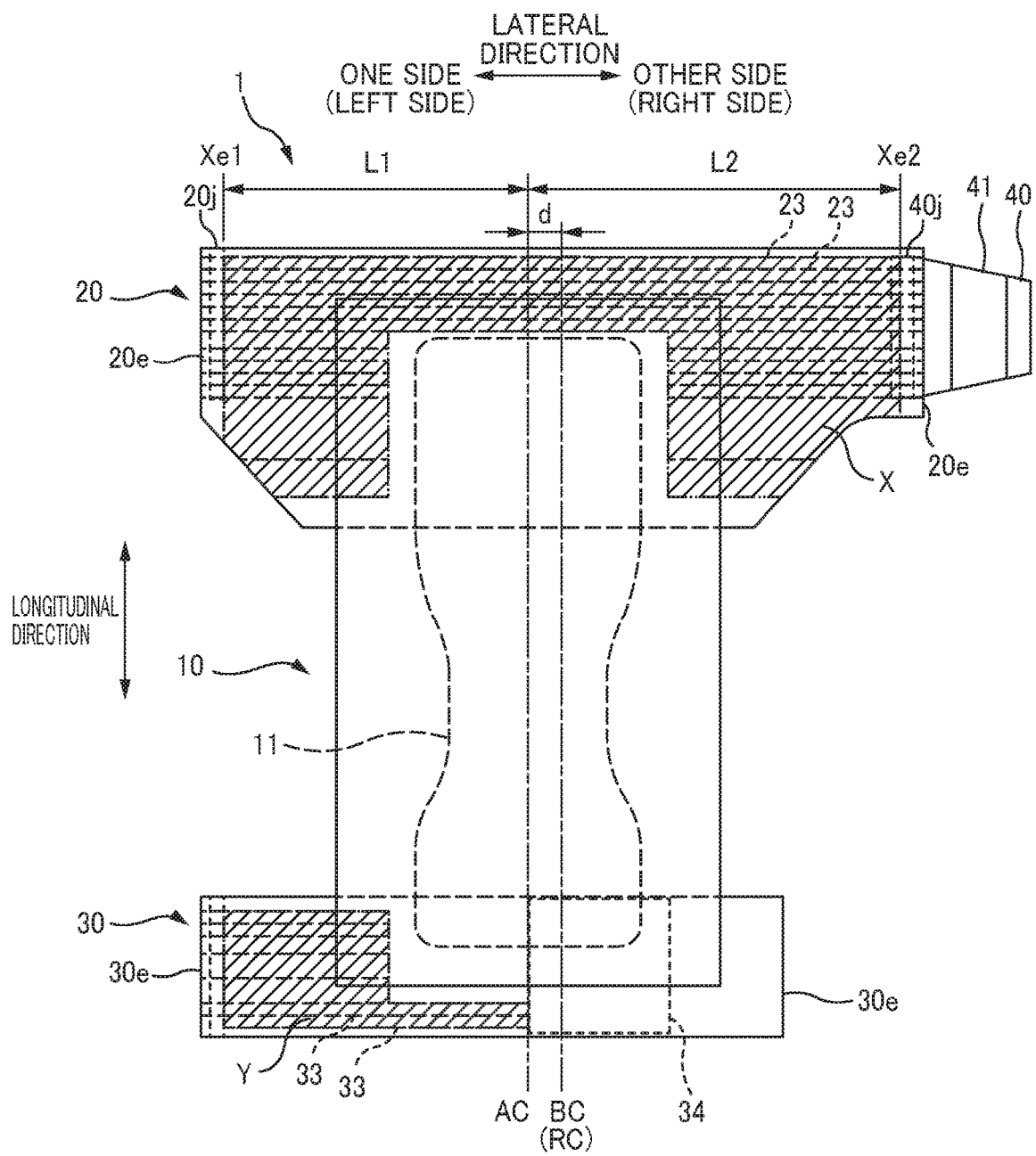
FIG. 3 is a diagram illustrating elastic regions X and Y.

The following describes the configuration of a diaper 1 according to the present embodiment. FIG. 1 is a schematic perspective view of a disposable diaper 1 (hereinafter referred to as a "diaper 1") associated with the present embodiment. FIG. 2 is a plan view of the diaper 1 in an unfolded state. The unfolded state is a state where a fastening portion 41 of the diaper 1 in FIG. 1 is detached from a target region 34, a joining portion 1b is uncoupled and opened, and the entirety of the diaper 1 is laid flat. FIG. 3 is a diagram illustrating elastic regions X and Y.

The diaper 1 according to the present embodiment is a disposable diaper mainly for use of infants or the like.

In the description below, the diaper 1 has a "longitudinal direction", a "lateral direction" that intersects the longitudinal direction", and a "front-back direction" that intersects the longitudinal direction and the lateral direction.

As shown in FIG. 1, the diaper 1 includes: an absorbent main body 10 (also called a "crotch portion") that is arranged at the crotch of the wearer and absorbs excrement; a back waist portion 20 that covers the back side of the wearer; and a front waist portion 30 that covers the stomach side of the wearer. The waist opening 1HB and a pair of leg openings 1HL and 1HL are formed. The diaper 1 in the unfolded state shown in FIG. 2 is folded in half with an approximately central position in the longitudinal direction serving as the folding position, and the lateral one-side end portions of the back waist portion 20 and the front waist portion 30 are joined together in the joining portion 1b.

The back waist portion 20 and the front waist portion 30 have an approximately rectangular planar shape, and in the unfolded state in FIG. 2, the back waist portion 20 and the front waist portion 30 are parallel with a space between each other in the longitudinal direction, and are bridged by the absorbent main body 10.

Also, the back waist portion 20 is fixed to one end portion 10a of the absorbent main body 10, and the front waist portion 30 is fixed to an other end portion 10b. The one end portion 10a is a region in which the absorbent main body 10 and the back waist portion 20 are stacked in the front-back direction (a first stacking region), and in FIG. 2, a rectangular region surrounded by lines A-B-C-D. The other end portion 10b is a region in which the absorbent main body 10 and the front waist portion 30 are stacked in the front-back direction (a second stacking region), and in FIG. 2, a rectangular region surrounded by lines F-G-H-I.

Structure of Absorbent Main Body 10

The absorbent main body 10 is approximately shaped as an elongated rectangle in a plan view, and is arranged at a central position in the lateral direction, with its lengthwise direction extending along the longitudinal direction of the diaper 1. In FIG. 2, a center line AC is the center of the absorbent main body 10 in the lateral direction. The absorbent main body 10 includes: an absorbent body 11 that absorbs and holds a liquid; a liquid-permeable top face sheet 12 that covers the absorbent body 11 on the wearer's skin side and allows the passage of excrement such as urine; and a liquid-impermeable back face sheet 13 that covers the absorbent body 11 on the non-skin side and prevents the leakage of a liquid from the non-skin side. The absorbent body 11 is constituted by liquid-absorbent fibers such as pulp fibers and is formed with a predetermined shape such as approximately a rectangular parallelepiped. The absorbent body 11 has a superabsorbent polymer incorporated therein. The absorbent main body 10 has barrier cuff portions preventing side leakage, and leg gather portions improving a fit around legs. But, for convenience, they are omitted in FIG. 2 or the like.

Structure of Back Waist Portion 20

The back waist portion 20 includes: a skin-side member 21 that is located on the wearer's skin side; a non-skin-side member 22 that is located on the non-skin side; and a plurality of elastic strings (elastic members) 23 that are located between the skin-side member 21 and the non-skin-side member 22. The skin-side member 21 and the non-skin-side member 22 are each a flexible sheet member that is constituted by a nonwoven fabric or the like. The elastic strings 23 are elastic members that give the back waist portion 20 lateral stretchability. And, a plurality of the elastic strings 23 are arranged extending along the lateral direction, and are fixed with an adhesive.

In FIGS. 2 and 3, the left side is the "one side", and the right side is "other side", and the center line RC indicates the lateral center of the back waist portion 20. A joining region 20j is provided in an end portion on the one side of the back waist portion 20, that is, in the left end portion of FIG. 2. The joining region 20j is joined to a joining region 30j (described later) of the front waist portion 30 by certain joining means (e.g., heat welding), forming a joining portion 1b of the diaper 1. Also, a fixing region 40j is provided in an end portion on the other side of the back waist portion 20, that is, in the right end portion of FIG. 2. The fastening member 40 (described later) is fixed to the fixing region 40j.

In the back waist portion 20, on the one side of its lower end 20b, provided is an inclined portion 20bl that is inclined toward the one-side end portion. On the other side of the lower end 20b, a straight portion 20bs and an inclined portion 20br are provided; the straight portion 20bs is substantially parallel with the lower end of the front waist portion 30, and the inclined portion 20br is on the laterally inward side of the straight portion 20bs and is symmetrical with the inclined portion 20bl about the center line AC. Due to the straight portion 20bs being substantially parallel with the lower end of the front waist portion 30, when the diaper 1 is worn by fastening the fastening portion 41 to the target region 34, the lower end of the front waist portion 30 can be aligned with the straight portion 20bs of the back waist portion 20. This improves the appearance of the diaper 1 when it is worn. By making the lateral length L6 of the inclined portion 20br larger than the lateral length L5 of the inclined portion 20*bl* (L6>L5), the inclination angle of the inclined portion 20*br* from the lower end 20*b* may be more moderate than that of the inclined portion 20*bl*.

The elastic strings 23 is each an elastic member which forms an elastic region X and which give the back waist portion 20 lateral stretchability, and improve the fit of the diaper 1. In the upper end portion of the back waist portion 20, the elastic strings 23 are continuous from the lateral one end of the absorbent main body 10 to the lateral other end. And, the elastic strings 23 are arranged continuously from the lateral end 20*e* of the back waist portion 20 on the one side to the lateral end 20*e* on the other side, extending along the lateral direction at a certain interval. Here, in the longitudinal central portion and the lower longitudinal end portion of the back waist portion 20, the back waist portion 20 is overlapped with the absorbent body 11. In that region, in the widthwise central portion of the back waist portion 20, in which the absorbent body 11 is provided, the elastic strings 23 are not provided. On the other hand, in the respective regions to the left and right of the absorbent body 11, the elastic strings 23 are provided substantially parallel with one another.

As shown in FIG. 3, the elastic region X is the region where the elastic strings 23 are provided, and extends from the laterally inward lateral end of the joining region 20*j* to the laterally inward lateral end of the fixing region 40*j*; as mentioned above, in the upper end portion of the back waist portion 20, the joining region 20*j* is provided on the one side, and the fixing region 40*j* is provided on the other side. In FIG. 3, the elastic region X is indicated by hatching. Note that for convenience in FIG. 3, hatching has been omitted for the joining regions 20*j* and 30*j* and the fixing region 40*j*. As shown in FIGS. 2 and 3, the elastic strings 23 extend to lateral ends 20*e* of the back waist portion 20. But, providing the joining region 20*j* and the fixing region 40*j* respectively in these lateral end portions of the back waist portion 20 makes it substantially impossible to exhibit stretching force of the following regions: the joining region 20*j*; the portion laterally outward of the joining region 20*j*; the fixing region 40*j*; and the portion laterally outward of the fixing region 40*j*. A one-side end Xe1 of the elastic region X is at the same position as the laterally inward end of the joining region 20*j*, and an other-side end Xe2 of the elastic region X is at the same position as the laterally inward end of the fixing region 40*j*. Here, the distance from the one-side end Xe1 of the elastic region X to the center line AC is defined as a distance L1, and the distance from the other-side end Xe2 of the elastic region X to the center line AC is defined as a distance L2. The distance L1 is smaller than the distance L2 (L1<L2).

In FIGS. 2 and 3, a center line BC indicates the approximate center of the body of a wearer when a wearer's leg has been inserted. In the present embodiment, the center line BC is at the same position as the center line RC that indicates the lateral center of the back waist portion 20. The center line RC and the center line BC are located different from the center line AC that indicates the center of the absorbent main body 10, and are to the right (on the other side) of the center line AC.

Here, the distance d between the center line RC of the back waist portion and the center line AC of the absorbent main body 10 is smaller than the difference between the distance L2 and the distance L1<L2−L1). More preferably two times the distance d (length 2d) is equal to or less than the difference between the distance L2 and the distance L1 (2d<L2−L1), and most preferably two times distance d is equal to the difference between the distance L2 and the distance L1 (2d=L2−L1).

The fastening member 40 is a tape substrate having a substantially trapezoidal shape, and is fixed to the back waist portion 20 in the fixing region 40*j* using a predetermined fixing means such as heat welding. The fastening member 40 has a fastening portion 41, which is a hook-and-loop fastener having a plurality of fastening projections (not shown) on its skin-side surface. The fastening projections of the fastening portion 41 are hooked to the target region 34 provided in the front waist portion 30, fastening the fastening member 40 to the front waist portion 30. The leg opening 1HL on the other side, and the waist opening 1HB are thus formed.

The length of a lateral end 20*e* of the back waist portion 20 on the other side is defined as a length H1, the longitudinal length of the fixing region 40*j* is defined as a length H2, and the length of the absorbent main body 10 from the lower end of one end portion 10*a* to the lower end of the other end portion 10*b* is defined as a length H3. The length H2 is larger than half the length H1 (H2>H1/2). The length H1 is smaller than half the length H3 (H1<H3/2).

Structure of Front Waist Portion 30

The front waist portion 30 includes: a skin-side member 31 that is located on the wearer's skin side; a non-skin-side member 32 that is located on the non-skin side; a plurality of elastic strings (elastic member) 33 that are located between the skin-side member 31 and the non-skin-side member 32; and the target region 34 on the non-skin-side surface of the front waist portion 30. The skin-side member 31 and the non-skin-side member 32 are each a flexible sheet member that is constituted by a nonwoven fabric or the like. The elastic strings 33 are elastic members that give the front waist portion 30 lateral stretchability. And, a plurality of the elastic strings 33 are arranged extending along the lateral direction, and are fixed to a sheet member with an adhesive. The target region 34 is a member capable of engaging with the fastening portion 41, and is made of nonwoven fabric.

As shown in FIG. 2, the front waist portion 30 has the joining region 30*j* in its left end portion, and the joining region 30*j* is joined to the joining region 20*j* of the back waist portion 20. In the front waist portion 30, the rectangular, target region 34 is provided in a region located right with respect to the center line AC of the absorbent main body 10.

The elastic strings 33 are elastic members that give the front waist portion 30 lateral stretchability, improving the fit of the diaper 1. In the front waist portion 30, the elastic strings 33 extend from a left lateral end 30*e* to the center line AC, but the elastic strings 33 are not provided in the range from a right lateral end 30*e* to the center line AC. However, even in a range from a left lateral end 30*e* to the center line AC, the elastic string 33 are not provided in a region overlapping with the absorbent body 11. As shown in FIG. 3, the elastic region Y is a region in which the elastic strings 33 are provided from the laterally inward end of the joining region 30*j* to the center line AC.

Here, the distance from the lateral end 30*e* of the front waist portion 30 on the one side to the center line AC is defined as a distance L3, and the distance from the lateral end 30*e* of the front waist portion 30 on the other side to the center line AC is defined as a distance L4. The distance L3 is larger than the distance L4 (L3>L4).

Also, the lateral length of the front waist portion 30 is smaller than the lateral length of the back waist portion 20. Specifically, in the lateral direction, the left, lateral end 30*e* of the front waist portion 30 is provided at substantially the same position as the left, lateral end 20*e* of the back waist portion 20. In contrast, in the lateral direction, the right, lateral end 30e of the front waist portion 30 is provided inside the right, lateral end 20e of the back waist portion 20.

Effectiveness of Diaper 1 according to the Present Embodiment

Figure 4A:
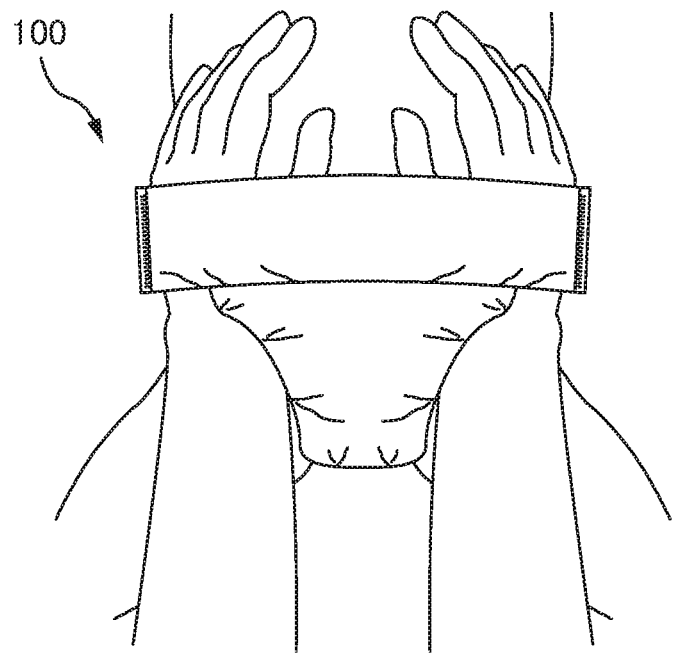
FIG. 4A is a diagram illustrating a method of putting on a conventional underpants-shaped diaper 100.

As a conventional disposable diaper, an underpants-shaped diaper 100 has been known. FIG. 4A is a diagram illustrating a method of putting on a conventional underpants-shaped diaper 100. As shown in FIG. 4A, when putting on the underpants-shaped diaper 100, enlarging widely the waist opening of the underpants-shaped diaper 100, then the wearer's legs are inserted through the respective leg openings, and finally the wearer's buttocks passes through the waist opening. Here, in order not to force the wearer to take unnatural posture, the wearer's legs have to be inserted at once through the respective leg openings. However, if a wearer such as an infant is wriggling his/her legs, it is difficult to insert his/her legs at once. Accordingly, in order to facilitate insertion of legs even if only slightly, the leg openings are enlarged. As for the waist opening, for passing the wearer's buttocks (larger than stomach) through, the waist opening is open widely to put on the diaper as shown in FIG. 4A. This makes the size of the leg openings and/or the waist opening larger than the wearer's stomach, and there is a possibility that the diaper does not fit to the wearer's legs and/or stomach.

Figure 4B:
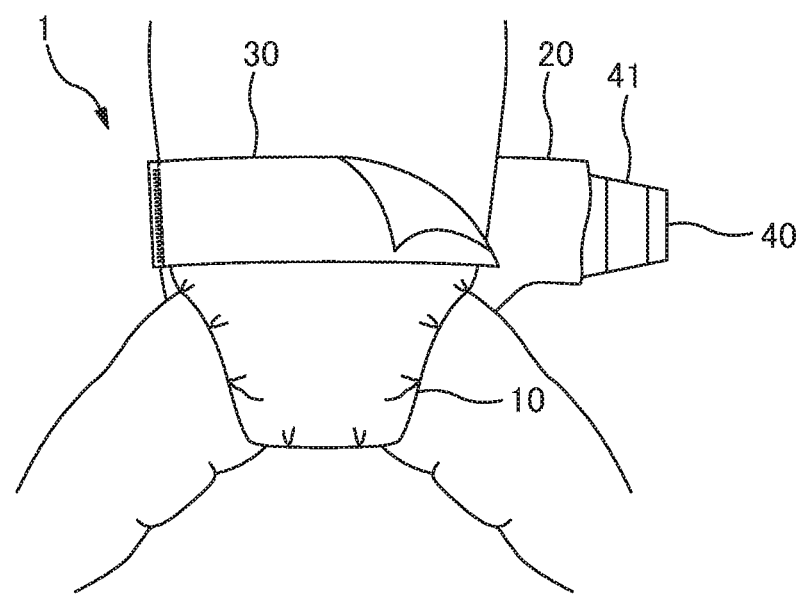
FIG. 4B is a diagram illustrating a method of putting on the diaper 1.

As opposed thereto, the diaper 1 according to the present embodiment can improve the fit of the waist opening and/or the leg openings 1HL, and can be put on more easily. FIG. 4B is a diagram illustrating a method of putting on the diaper 1. In the diaper 1, the joining portion 1b is formed in the one-side end portion, and the fastening member 40 is formed in the other-side end portion. First, an operator inserts a wearer's one leg into the diaper 1 on the one side, the leg on the one side (the wearer's right leg in the present embodiment) is positioned at a position when the diaper 1 is put on; in other words, the leg opening 1HL on the one side is positioned on a hip joint of the wearer's right leg as shown in FIG. 4B. Thereafter, the operator presses the other-side end portion of the front waist portion 30 against the skin side by his/her hand, and pulls the fastening member 40 by his/her other hand. Then, the operator fastens the fastening portion 41 to the target region 34 of the front waist portion 30, forming the leg opening on the other side and putting the diaper 1 on the wearer. This method for putting on makes it unnecessary to insert legs into the leg openings at once, unlike a conventional method. It is easier to insert one leg into a leg opening 1HL on the one side compared to inserting legs the leg openings 1HL at once, and therefore it is possible to easily put the diaper 1 on an infant even if the infant is wriggling their legs.

Here, assuming that, in the elastic region X, the distance L1 from the one-side end Xe1 to the center line AC of the absorbent main body 10 is equal to the distance L2 from the other-side end Xe2 to the center line AC. In this case, the back waist portion 20 is stretched in the lateral direction due to the fastening member 40 being pulled, and therefore the absorbent body 10 will shift on the other side and be displaced from a substantial center of the wearer's body. Consequently, there is a possibility of leakage of excrement, and of wearer's discomfort.

Figure 5A:
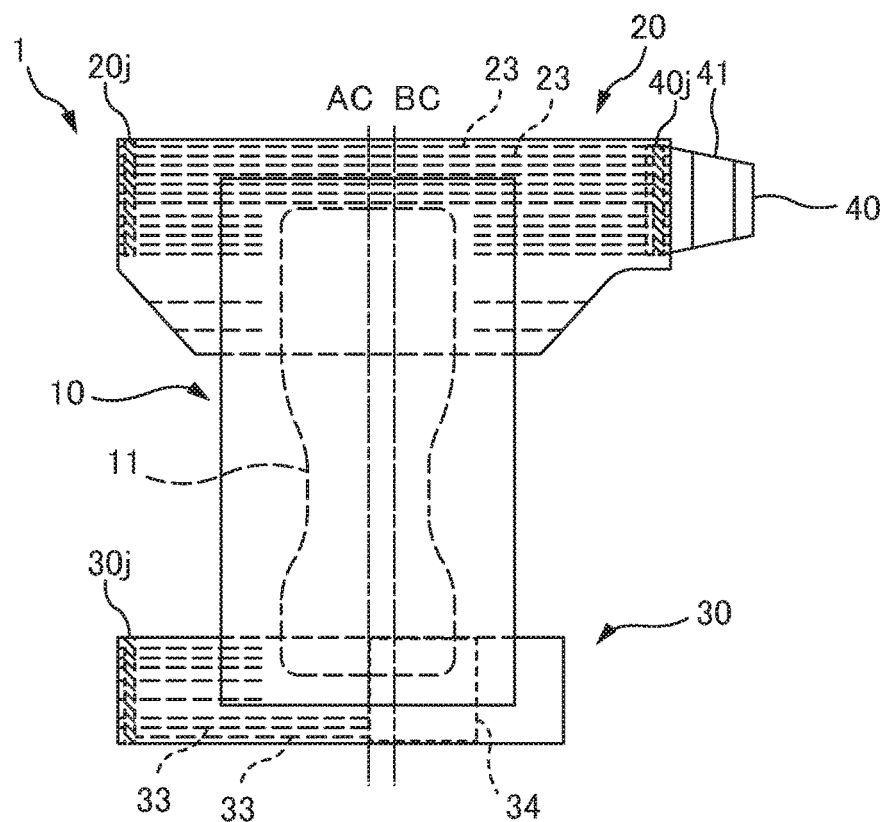
FIG. 5A is a plan view of the diaper 1 in an unfolded manner, when a wearer's leg has been inserted to the diaper 1.
Figure 5B:
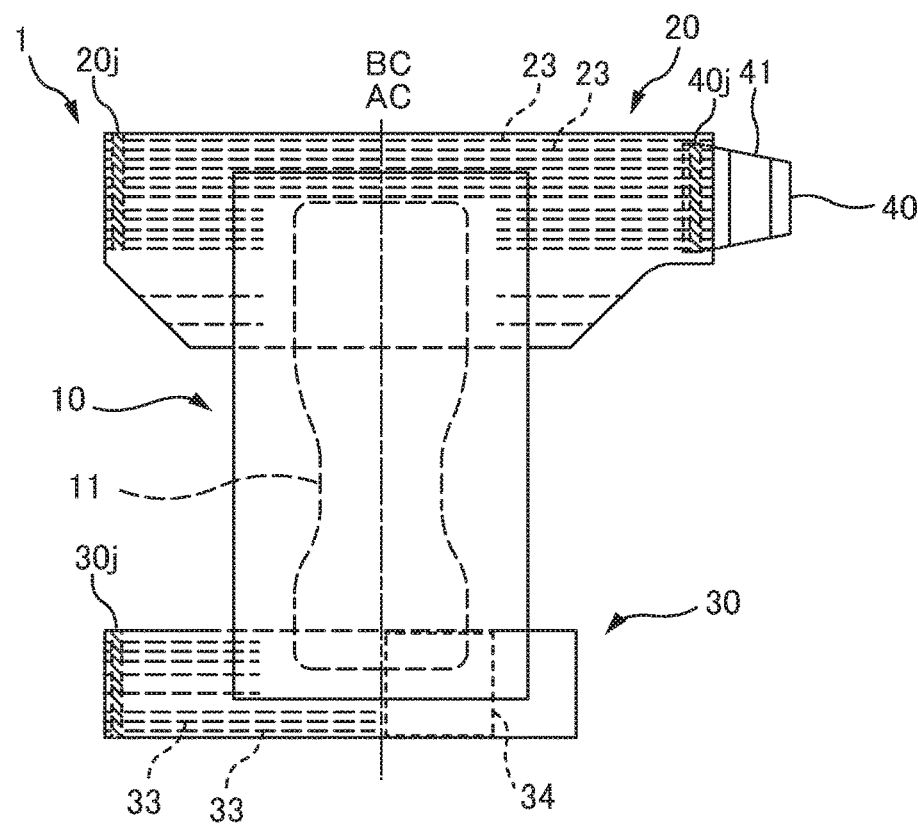

In the diaper 1 according to the present embodiment, anticipating that the lateral center of the absorbent main body 10 is positioned away from a substantial center of the wearer's body, the elastic region X is formed so that the distance L1 from the one-side end Xe1 to the center line AC of the absorbent main body 10 is smaller than the distance L2 from the other-side end Xe2 to the center line AC. FIG. 5A is a plan view of the diaper 1 in an unfolded manner, when a wearer's leg has been inserted to the diaper 1. FIG. 5B is a plan view of the diaper 1 in an unfolded manner, when the diaper 1 is put on. As shown in FIG. 5A, in a state where a wearer's leg has been inserted to the diaper 1, the center line AC of the absorbent main body 10 is located on the one side (the side of the wearer's right leg in the present embodiment) of the center line BC that indicates a substantial center of the wearer's body. In this state, the fastening member 40 is pulled to the other side, and the fastening portion 41 is fastened to the front waist portion 30, forming the diaper 1 into a shape when it is worn. Then, the back waist portion 20 stretches in the lateral direction, and the absorbent main body 10 moves to the other side, that is, the side of the wearer's left leg. Accordingly, the center line AC and the center line BC approach each other, and the absorbent main body 10 can be brought near the center of the body of the wearer. In an ideal positional relation, as shown in FIG. 5B, the center line AC is aligned with the center line BC, that is, the lateral center of the absorbent main body 10 of the diaper 1 is aligned with the center of the wearer's body.

In the diaper 1, it is possible for the elastic region X to be formed so that the distance L1 from the one-side end Xe1 to the center line AC of the absorbent main body 10 is different from the distance L2 from the other-side end Xe2 to the center line AC. Accordingly, the distance L1 on the one side can be set to a length suitable to the leg opening 1HL according to the size of a leg on the one side (the right leg in the present embodiment), making it possible to improve the fit of the leg opening 1HL on the one side. In addition, fastening by the fastening portion 41 can adjust the leg opening 1HL for a leg on the other side (the left leg in the present embodiment), making it possible to ensure the fit of the leg opening 1HL on the other side.

Further, in the present embodiment, the region of the front waist portion 30 from the one-side end portion to the center line AC includes the elastic region Y extending along the lateral direction; and the region of the front waist portion 30 from the other-side end portion to the center line AC does not include an elastic region. This improves the fit of the diaper 1. The region of the front waist portion 30 from the other-side end portion to the center line AC is a region to which the fastening portion 41 of the fastening member 40 is fastened. Accordingly, it is for reducing a possibility that, if elastic members (e.g., the elastic strings 33) are arranged in this region, stretching/contraction of the elastic members makes it easier to remove the foregoing fastening. In this case, the target region 34 is arranged in a part of the front waist portion 30 in which no elastic region exists. Note that the region of the front waist portion 30 from the other-side end portion to the center line AC may include an elastic region.

Further, in the present embodiment, the lateral distance L3 between the center line AC and the one-side end of the longitudinal upper end of the front waist portion 30 is larger than the lateral distance L4 between the center line AC and the other-side end of the longitudinal upper end of the front waist portion 30 (L3>L4). This can make smaller a region of the front waist portion 30 on which the back waist portion 20 is stacked in the front-back direction when the fastening portion 41 located on the other side is fastened to the front waist portion 30. This makes it possible to reduce discomfort caused by stacking the back waist portion 20 and the front waist portion 30 when the wearer puts on the diaper.

Further, in the present embodiment, the lateral distance d from the center line RC of the back waist portion 20 to the center line AC of the absorbent main body 10 is made smaller than the difference between the distance L2 of the elastic region X from the other-side end Xe2 to the center line AC and the distance L1 of the elastic region X from the one-side end Xe1 to the center line AC (d<L2−L1). This can reduce a possibility that when fastening the fastening portion 41 to the front waist portion 30, the lateral center of the absorbent main body 10 (the center line AC) becomes positioned away from the substantial center of a human body (the center line BC). In the present embodiment, the center line BC indicating the substantial center of a human body is at the same position as the center line RC indicating the lateral center of the back waist portion 20. However, the present invention is not limited thereto. The position of the center line BC may be appropriately adjusted depending on the size of wearer's body, the dimensions of components, the stretching force of elastic members, or the like. And, the position of the center line BC may be different the position of the center line RC.

As mentioned above, in the diaper 1, the stretching force of the elastic strings 33 does not work in a region of the front waist portion 30 on which the back waist portion 20 and/or the fastening member 40 are stacked. Here, the stretching force of each elastic string 23 is equal to the stretching force of each elastic string 33; and the center line BC indicating the substantial center of a human body is at the same position as the center line RC indicating the lateral center of the back waist portion 20, making two times distance d equal to the difference between the distance L2 and the distance L1 (2d=L2−L1). This configuration realizes the most ideal positional relation allowing the elastic strings 23 and 33 to produce appropriate fit of the waist opening 1HB.

Figure 6:
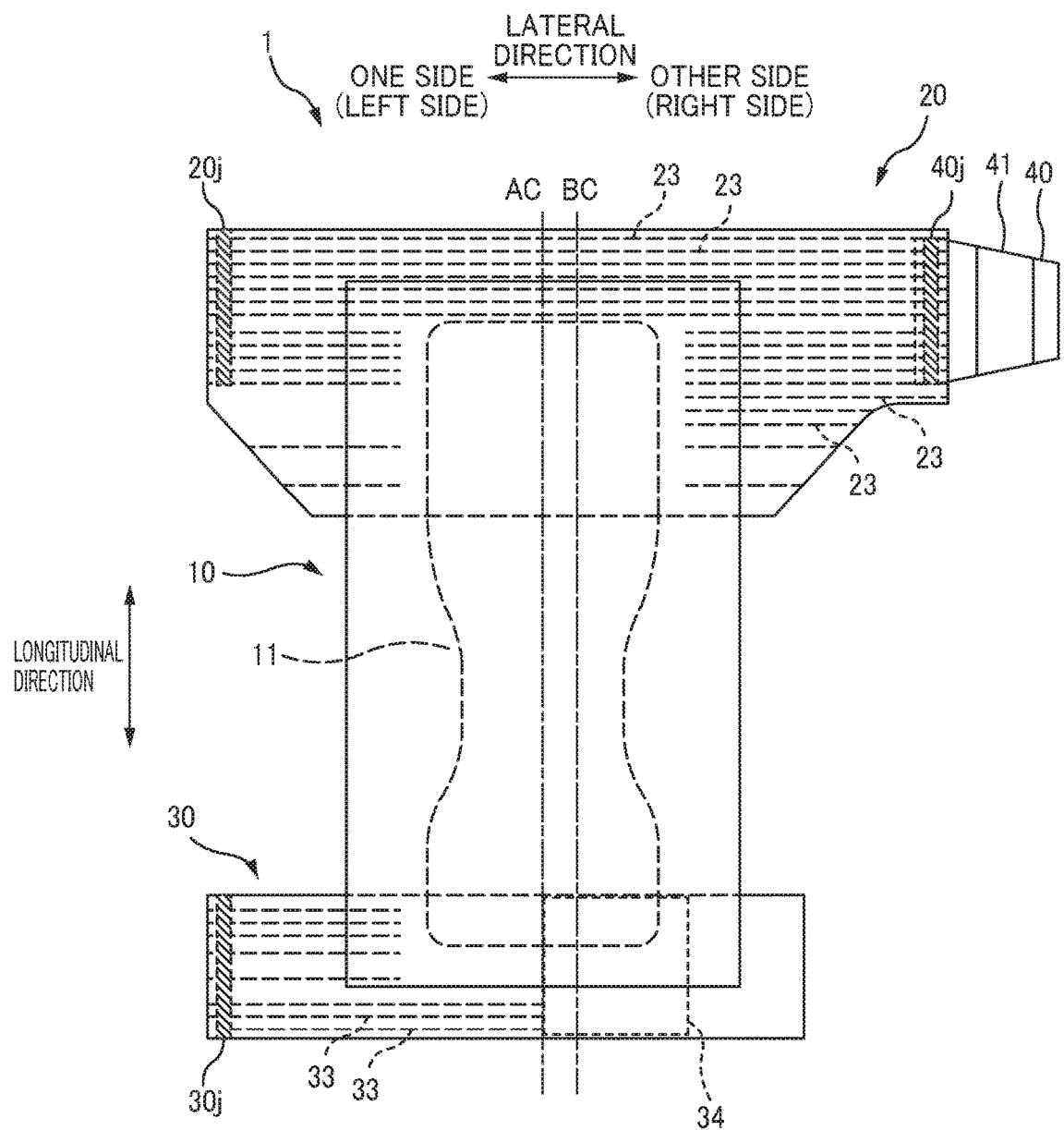
FIG. 6 is a plan view of the diaper 1 in an unfolded state, the diaper 1 having a larger number of elastic strings on a side of a fastening member 40.

Further, in the elastic region X of the back waist portion 20 in which a plurality of elastic strings 33 are provided, the number of the elastic strings 33 between the other-side end Xe2 and the center line AC may be larger than the number of the elastic strings 33 between the one-side end Xe1 and the center line AC. FIG. 6 is a plan view of the diaper 1 in an unfolded state, the diaper 1 having the larger number of the elastic strings on a side of the fastening member 40. As shown in FIG. 6, in the diaper 1, a part of the front waist portion 30 on the other side relative to the center line AC is fastened by the fastening portion 41, and therefore the elastic string 33 is not provided in the part. Even if there are elastic strings 33 in this region, there is a possibility that stretchability deteriorates due to fastening by the fastening portion 41, lowering the stretchability of the part on the other side during a period when putting on the diaper 1, compared to a part on the one side. And, a larger number of the elastic strings 33 are provided between the other-side end Xe2 and the center line AC, making it possible to improve the fit of the diaper 1.

Figure 7A:
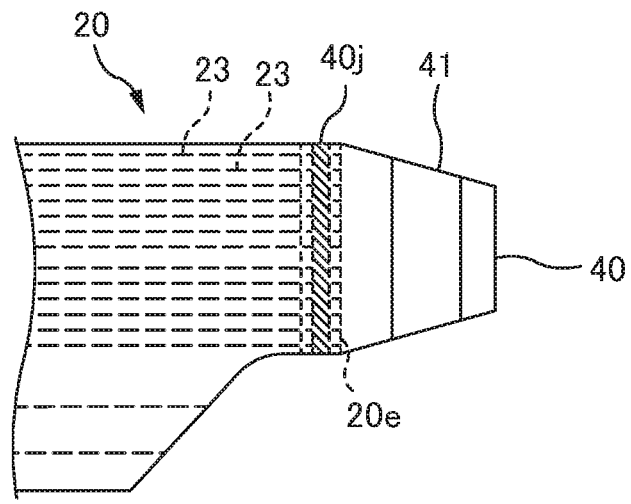
FIG. 7A is a diagram showing an example of the shape of the fastening member 40.

Further, in the present embodiment, the back waist portion 20 includes the fastening member 40 having the fastening portion 41, and the fastening member 40 is fixed to the other-side end portion the back waist portion 20, in the fixing region 40j of the back waist portion 20. The longitudinal length H2 of the fixing region 40j is set equal to or larger than half the length H1 of the lateral end 20e of the back waist portion 20 on the other side (H2>H1/2). Accordingly, when the fastening member 40 is pulled from the state of FIG. 4B, and is fastened to the front waist portion 30, it is possible to give the force of pulling the fastening member 40 to a not-less-than-half part of the lateral end 20e of the back waist portion 20 on the other side. This makes it possible to apply more evenly-distributed force to the front waist portion 30, reducing a possibility of break and deformation of the front waist portion 30, which will be caused by applying excessive force to a part of the front waist portion 30. FIG. 7A is a diagram showing an example of the shape of the fastening member 40. As shown in FIG. 7A, it is more preferable that the longitudinal length of the fixing region 40j is substantially equal to the length of the lateral end 20e of the back waist portion 20 on the other side.

Further, the following configuration may be employed: the back waist portion 20, the front waist portion 30 and the absorbent main body 10 are individual components; in the back waist portion 20, on the one side of the lower end 20b, provided is the inclined portion 20bl that is inclined toward the one-side end portion; on the other side of the lower end 20b, provided is the inclined portion 20br that is inclined toward the other-side end portion; and the lateral length L5 of the inclined portion 20bl is larger than the lateral length L6 of the inclined portion 20br (L6>L5). The lateral length L5 of the inclined portion 20bl on the one side is set to a length according to the size of the circumference of a wearer's leg, improving the fit of the leg opening 1HL on the one side to a wearer's leg. And, the lateral length L6 of the inclined portion 20br on the other side may be larger than the lateral length L5 of the inclined portion 20bl on the one side, adjusting the size of the leg opening 1HB on the other side by fastening by the fastening portion 41 when putting on the diaper.

In the present embodiment, the back waist portion 20, the front waist portion 30 and the absorbent main body 10 are individual components. The absorbent main body 10 has a one end portion 10a on its back side in the front-back direction, and the one end portion 10a is placed on the back waist portion 20. Also, the absorbent main body 10 has an other end portion 10b on its front side in the front-back direction, and the other end portion 10b is placed on the front waist portion 30. the length H1 of a lateral end 20e of the back waist portion 20 on the other side is smaller than half the length H3 of the absorbent main body 10 from the lower end of the one end portion 10a to the lower end of the other end portion 10b (H3/2>H1). Making relatively longer the length H3 of the absorbent main body 10 from the lower end of the one end portion 10a to the lower end of the other end portion 10b makes it possible for the leg openings 1HL to have a length according to the size of the legs. In addition, making shorter the length of the other-side end 20e of the back waist portion 20 makes it easier to transmit to the back waist portion 20 a force of pulling the fastening member 40 when fastening, making it easier to put on the diaper.

In the present embodiment, in the upper end portion of the back waist portion 20, the elastic region X are laterally continuous at least from the one end of the absorbent main body 10 to the other end, making it possible to reduce a possibility that, when fastening the fastening portion 41 to the front waist portion 30, the lateral center of the absorbent main body (the center line AC) is misaligned with the lateral center of the wearer's crotch (the center line BC).

Other Embodiments

Although an embodiment of the present invention has been described above, the above embodiment is for facilitating the understanding of the present invention, and is not to be construed as limiting the present invention. The present invention can be modified, improved, etc. without departing from the gist of the present invention, and equivalents of the present invention are also encompassed within the present invention. For example, modifications such as the following can be made.

Although the above embodiment illustrates the so-called three piece type of disposable diaper 1 as an example of the absorbent article, there is no limitation whatsoever to this. For example, the absorbent article may be a two piece type of disposable diaper including: a first component is an exterior sheet including a back waist portion and a front waist portion that are connected via a crotch portion as a single unit; and a second component is an absorbent main body that is fixed to the skin-side surface of the exterior sheet.

Figure 7B:
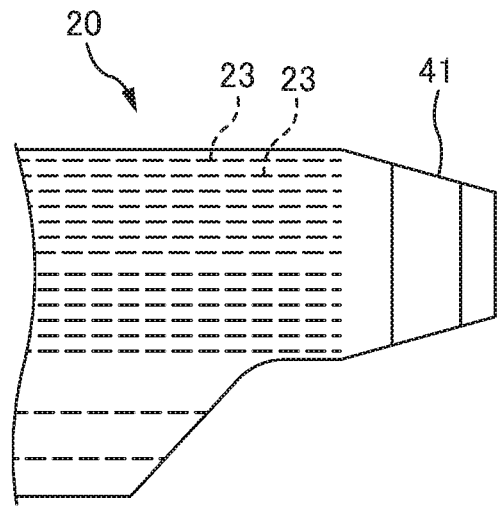
FIG. 7B is a diagram showing an example of the shape of the fastening portion 41.

In the foregoing embodiment, the back waist portion 20 and the fastening member 40 are separated components. However, the present invention is not limited thereto. FIG. 7B is a diagram showing an example of the shape of the fastening portion 41. It is also acceptable that the back waist portion 20 and the fastening member 40 are formed as a single identical member, providing the fastening portion 41 which projects in the lateral direction from a region of the back waist portion 20 in which the elastic strings 23 are arranged, as shown in FIG. 7B.

The above embodiment describes the state where the fastening member 40 projects in a lateral direction from the back waist portion 20 when the diaper is put on. However, the fastening member 40 may be folded when the disposable diaper 1 is manufactured, or the fastening member 40 may be provisionally connected to the front waist portion 30 by perforations.

Also, in the above embodiment, although the elastic region X for ensuring the fit of the diaper 1 is provided, a configuration is possible in which the elastic region X is provided in only the upper end portion of the back waist portion 20. Even with this configuration, it is possible to ensure a necessary fit for the waist opening BIB of the diaper 1.

In the above embodiment, although the elastic strings 23 and 33 are used as the elastic members, there is no limitation to this. It is possible to use a nonwoven fabric that has stretchability, for example.

In the above embodiment, although the elastic strings 23 and 33 are not provided in the overlapping regions of the back waist portion 20 and the front waist portion 30 in which they overlap with the absorbent body 11, there is no limitation to this. The elastic strings 23 and 33 may be provided in the regions overlapping with the absorbent body 11. By not providing the elastic strings 23 and 33 in the regions overlapping with the absorbent body 11, it is possible to reduce the risk of the absorbent body 11 deformed due to stretching and contracting of the elastic strings 23 and 33. However, by providing the elastic strings 23 and 33 in the regions overlapping with the absorbent body 11, it is possible to improve the fit of the absorbent main body 10 through stretching force.

The invention claimed is:

1. An absorbent article having a longitudinal direction, a lateral direction intersecting the longitudinal direction, and a front-back direction intersecting the longitudinal direction and the lateral direction,
   the absorbent article comprising:
   a front waist portion extending along the lateral direction;
   a back waist portion extending along the lateral direction; and
   a crotch portion provided between the front waist portion and the back waist portion,
   a one-side end portion of the back waist portion on a one side in the lateral direction being joined to a one-side end portion of the front waist portion on the one side in the lateral direction,
   the back waist portion including a fastening portion on another side in the lateral direction,
   when putting on the absorbent article, the fastening portion projecting laterally from the back waist portion and being capable of being fastened to the front waist portion,
   the back waist portion including an elastic region in at least an upper end portion,
   the elastic region extending along the lateral direction,
   a lateral distance between a lateral one-side end of the elastic region on the one side and a lateral center of the crotch portion being smaller than a lateral distance between a lateral other-side end of the elastic region on the other side and the lateral center of the crotch portion.

2. An absorbent article according to claim 1,
   wherein in the front waist portion,
   a region from the one-side end portion to the lateral center of the crotch portion includes an elastic region extending along the lateral direction,
   a region from an other-side end portion to the lateral center of the crotch portion does not include an elastic region.

3. An absorbent article according to claim 1, wherein
   a lateral distance between the lateral center of the crotch portion and a lateral one-side end of a longitudinal upper end of the front waist portion
   is larger than
   a lateral distance between the lateral center of the crotch portion and a lateral other-side end of the longitudinal upper end of the front waist portion.

4. An absorbent article according to claim 1, wherein
   a lateral distance from a lateral center of the back waist portion to the lateral center of the crotch portion
   is smaller than
   a difference between a lateral distance from the lateral other-side end of the elastic region to the lateral center of the crotch portion and the lateral distance from the lateral one-side end of the elastic region to the lateral center of the crotch portion.

5. An absorbent article according to claim 1, wherein
   in the back waist portion,
   the elastic region comprises a first elastic region between the lateral other-side end of the elastic region and the lateral center of the crotch portion and a second elastic region between the lateral one-side end of the elastic region and the lateral center of the crotch portion,
   a number of elastic strings in the first elastic region
   is larger than
   a number of elastic strings in the second elastic region.

6. An absorbent article according to claim 1, wherein
   the back waist portion includes a fastening member having the fastening portion,
   the fastening member is fixed to an other-side end portion of the back waist portion in a fixing region of the back waist portion, and
   a longitudinal length of the fixing region is equal to or larger than half a longitudinal length of an other-side end of the back waist portion.

7. An absorbent article according to claim 1, wherein
   the back waist portion, the front waist portion, and the crotch portion are individual components,
   a lower end of the back waist portion includes on the one side a one-side inclined portion that is inclined toward the lateral one-side end, the lower end of the back waist portion includes on the other side an other-side inclined portion that is inclined toward the lateral other-side end, and a lateral length of the one-side inclined portion is larger than a lateral length of the other-side inclined portion.

8. An absorbent article according to claim 1, wherein the back waist portion, the front waist portion, and the crotch portion are individual components, a first stacking region in which the crotch portion and the back waist portion are stacked is provided in a back side of the crotch portion in the front-back direction, a second stacking region in which the crotch portion and the front waist portion are stacked is provided in a front side of the crotch portion in the front-back direction, and a length of a other-side end of the back waist portion is smaller than half a length of the crotch portion from a lower end of the first stacking region to a lower end of the second stacking region.

9. An absorbent article according to claim 1, wherein the elastic region in the upper end portion is continuous in the lateral direction at least from a one end of the crotch portion to another end of the crotch portion.

\* \* \* \* \*